(12) United States Patent
Ghersi

(10) Patent No.: US 11,690,751 B2
(45) Date of Patent: Jul. 4, 2023

(54) ADJUSTABLE NASAL MOLDING SPLINT

(71) Applicant: Marcelo Ghersi, Coral gables, FL (US)

(72) Inventor: Marcelo Ghersi, Coral gables, FL (US)

(*) Notice: Subject to any disclaimer, the term of this patent is extended or adjusted under 35 U.S.C. 154(b) by 44 days.

(21) Appl. No.: 17/565,246

(22) Filed: Dec. 29, 2021

(65) Prior Publication Data

US 2022/0233340 A1 Jul. 28, 2022

Related U.S. Application Data

(60) Provisional application No. 63/141,266, filed on Jan. 25, 2021.

(51) Int. Cl.
*A61F 5/08* (2006.01)
(52) U.S. Cl.
CPC ...................................... *A61F 5/08* (2013.01)
(58) Field of Classification Search
CPC .... A61M 16/0666; A61F 5/05891; A61F 5/08
USPC ........................................................ 606/199
See application file for complete search history.

(56) References Cited

U.S. PATENT DOCUMENTS

| | | | |
|---|---|---|---|
| 2,509,157 | A | 5/1950 | Lind |
| 3,935,859 | A | 2/1976 | Doyle |
| 4,378,802 | A | 4/1983 | Ersek |
| 5,931,799 | A | 8/1999 | Guastella |
| 8,801,751 | B2 | 8/2014 | Kaczperski et al. |
| 8,858,477 | B2 | 10/2014 | Pylyp |
| 9,381,332 | B2 | 7/2016 | Judd |
| 2008/0082030 | A1 | 4/2008 | Clark |
| 2010/0042139 | A1 | 2/2010 | Honegger |
| 2022/0104961 | A1* | 4/2022 | Chasan ............... A61F 5/05891 |

* cited by examiner

*Primary Examiner* — Majid Jamialahmadi
(74) *Attorney, Agent, or Firm* — Mark Terry

(57) ABSTRACT

A medical device for facilitating post-operative nasal reshaping includes a nose splint comprising a rigid curved surface shaped to fit over a dorsum of a patient's nose, the nose splint having a proximal surface and a distal surface; a tubular sleeve hingably attached to the distal surface of the nose splint; a pair of malleable arms movably coupled to the tubular sleeve, the pair of malleable arms configured to extend into a supratip of the patient's nose via the patient's nostrils; and an adjustable thumb nut coupled to the tubular sleeve and the pair of malleable arms, wherein the thumb nut is configured such that adjustment of the thumb nut moves the pair of malleable arms in a direction orthogonal to the distal surface of the nose splint.

20 Claims, 5 Drawing Sheets

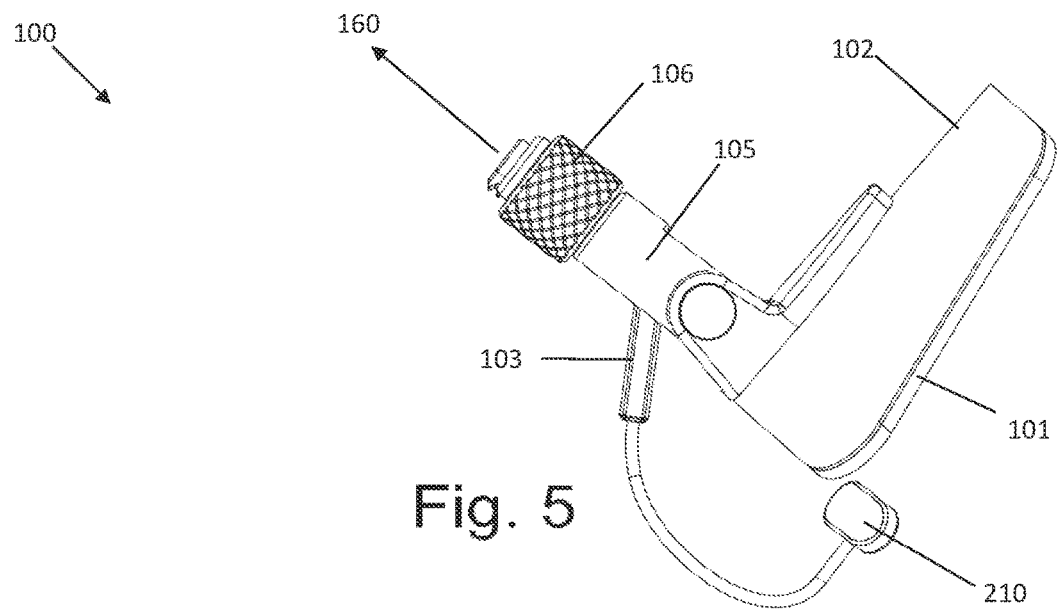
Fig. 5
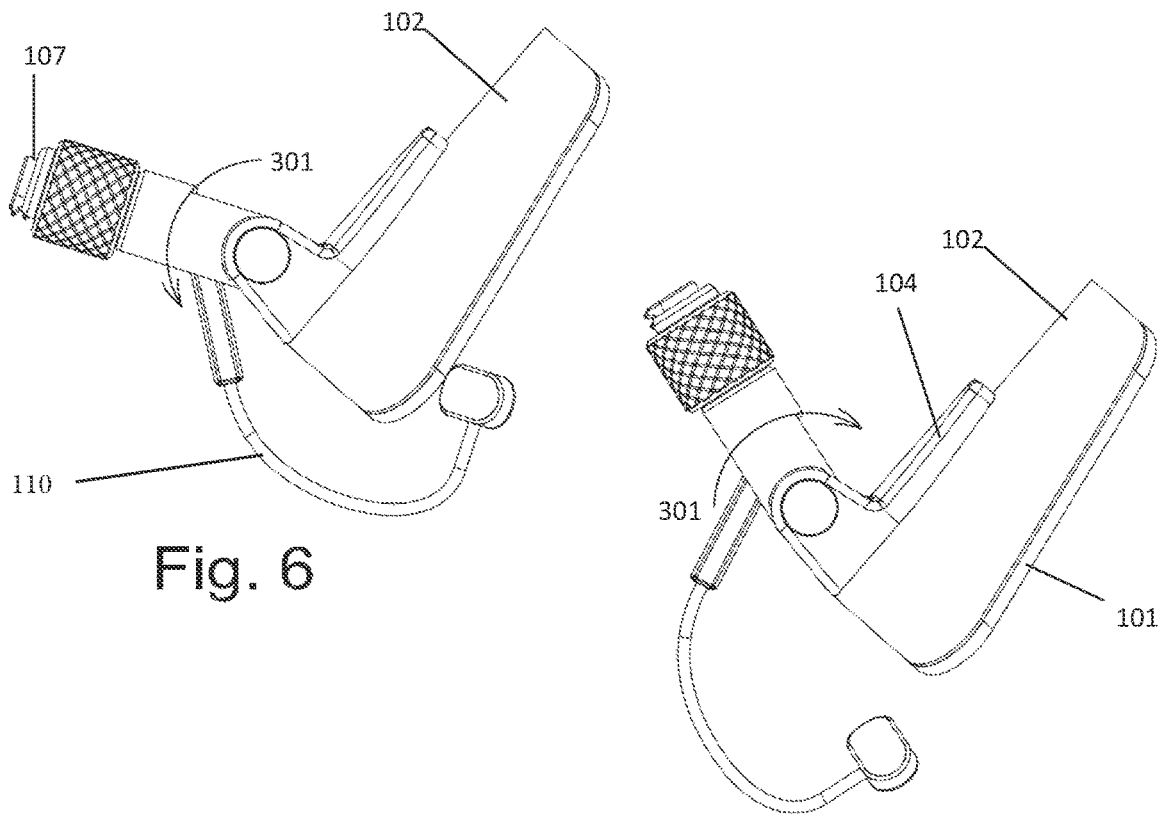
Fig. 6
Fig. 7

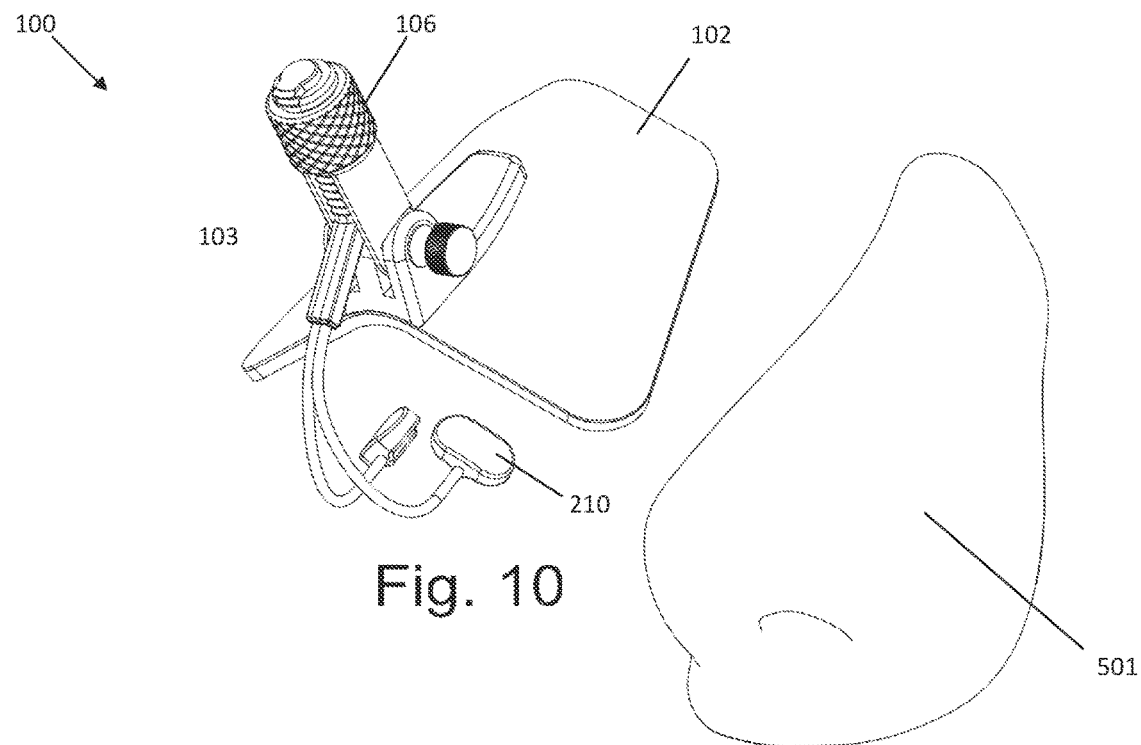
Fig. 10
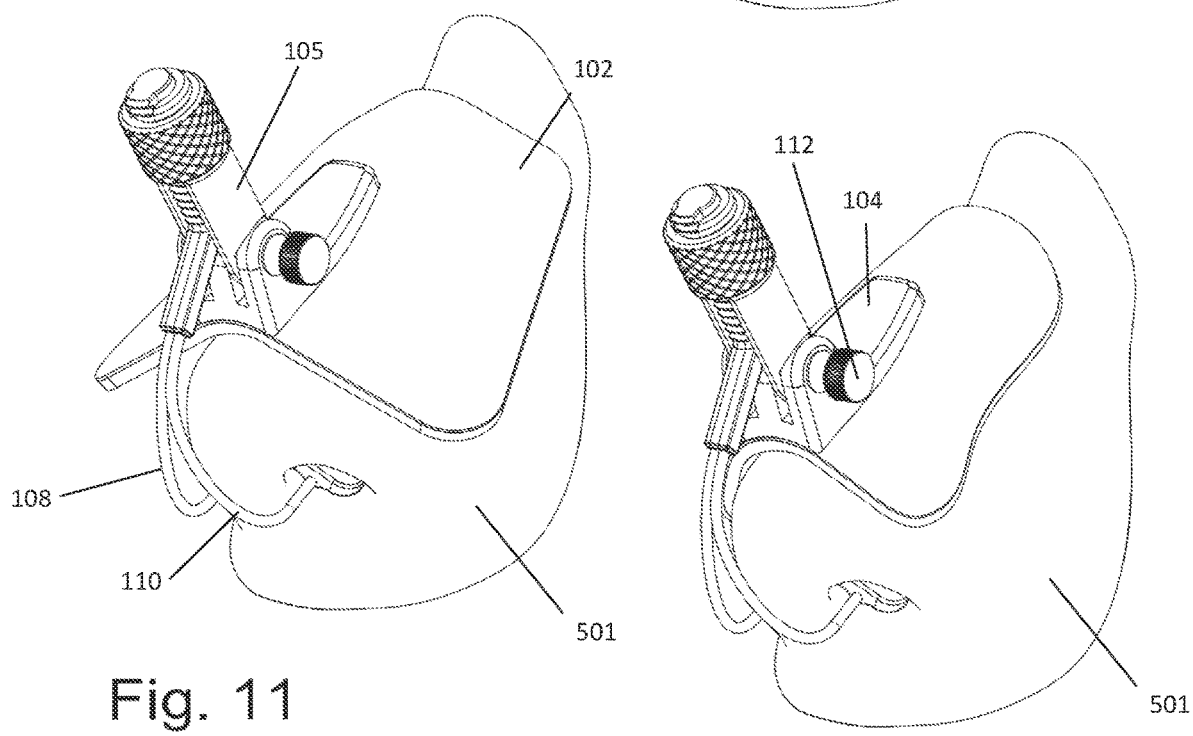
Fig. 11
Fig. 12

ADJUSTABLE NASAL MOLDING SPLINT

CROSS-REFERENCE TO RELATED APPLICATIONS

This patent application claims priority to provisional patent application 63/141,266 filed Jan. 25, 2021, and titled "Adjustable Nasal Molding Splint." Provisional patent application 63/141,266 is hereby incorporated by reference in its.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

TECHNICAL FIELD

The technical field relates generally to medical devices and, more specifically, to post-operative medical devices.

BACKGROUND

Rhinoplasty, or nasal surgery, typically brings about changes in the shape and size of the nose. Once the procedure is completed, the clinician uses taping and splinting devices to maintain the shape attained during surgery, in order to prevent the inflammatory and healing processes from affecting the surgical results.

Splinting devices work by stabilizing fractured nasal bones, much like a cast, so that they heal in the position desired by the surgeon. Nasal splints also protect the nose and surrounding areas from possible injury after surgery, when the nose is most vulnerable to trauma and damage. Taping techniques are more varied, and aim to stabilize the cartilaginous nasal tip, in order to protect the achieved rotation and projection of the nose.

Splinting devices work relatively well, but taping techniques are only minimally helpful and rarely offset the powerful forces that come about during the healing stages of nasal surgery. The result of this is long term results that differ from the results obtained during surgery. Scarring, fibrosis, and inflammation can and typically do change the shape of the nose despite the use of taping devices. To date, there is no device that allows a rhinoplasty surgeon to offset unfavorable healing and help maintain rotation and projection of the tip of the nose, as well as stabilization of the bony pyramid. The current drawback of conventional splinting and taping techniques is that they do not allow for much molding of the nasal tip, supra tip and dorsum.

Therefore, a need exists for improvements over the current devices, and particularly for a more adaptable post-operative nasal splint that allows the surgeon to mold the nasal tip, supra tip and dorsum for better and more reproducible surgical results, as well as a nasal splint that allows for the prevention of movement of tissue and cartilage in different directions.

SUMMARY

A more efficient medical device for facilitating post-operative nasal reshaping is provided. The device allows the clinician to adjust nasal tip rotation and projection as needed, in addition to osseous and soft tissue stabilization during the critical postoperative healing period. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

In one embodiment, a medical device for facilitating post-operative nasal reshaping includes a nose splint comprising a rigid curved surface shaped to fit over a dorsum of a patient's nose, the nose splint having a proximal surface and a distal surface; a tubular sleeve hingably attached to the distal surface of the nose splint; a pair of malleable arms movably coupled to the tubular sleeve, the pair of malleable arms configured to extend into a supratip of the patient's nose via the patient's nostrils; and an adjustable thumb nut coupled to the tubular sleeve and the pair of malleable arms, wherein the thumb nut is configured such that adjustment of the thumb nut moves the pair of malleable arms in a direction orthogonal to the distal surface of the nose splint.

In another embodiment, the medical device for facilitating post-operative nasal reshaping includes a nose splint comprising a rigid curved surface shaped to fit over a dorsum of a patient's nose, the nose splint having a distal surface and a proximal surface configured for application to the patient's nose, a tubular sleeve hingably attached to a hinge protruding from the distal surface of the nose splint, a pair of malleable arms movably coupled to the tubular sleeve, the pair of malleable arms configured to extend into a supratip of the patient's nose via the patient's nostrils, and an adjustable thumb nut coupled to the tubular sleeve and the pair of malleable arms, wherein the thumb nut is configured such that adjustment of the thumb nut moves the pair of malleable arms in a direction orthogonal to the distal surface of the nose splint.

BRIEF DESCRIPTION OF THE DRAWINGS

The accompanying drawings, which are incorporated in and constitute a part of this disclosure, illustrate various example embodiments. In the drawings:

FIG. 5 is a right-side view of the post-operative nasal splint, according to an example embodiment;

FIG. 6 is a right-side view of the post-operative nasal splint, showing the tubular element in a rotated downwards position, according to an example embodiment;

FIG. 7 is a right-side view of the post-operative nasal splint, showing the tubular element in a rotated upwards position, according to an example embodiment;

FIG. 10 is a bottom perspective view of the post-operative nasal splint before application to a patient's nose, according to an example embodiment;

FIG. 11 is a bottom perspective view of the post-operative nasal splint after application to a patient's nose, according to an example embodiment;

FIG. 12 is a bottom perspective view of the post-operative nasal splint after application to a patient's nose and after the splint has been formed, according to an example embodiment.

DETAILED DESCRIPTION

Figures 1, 2:
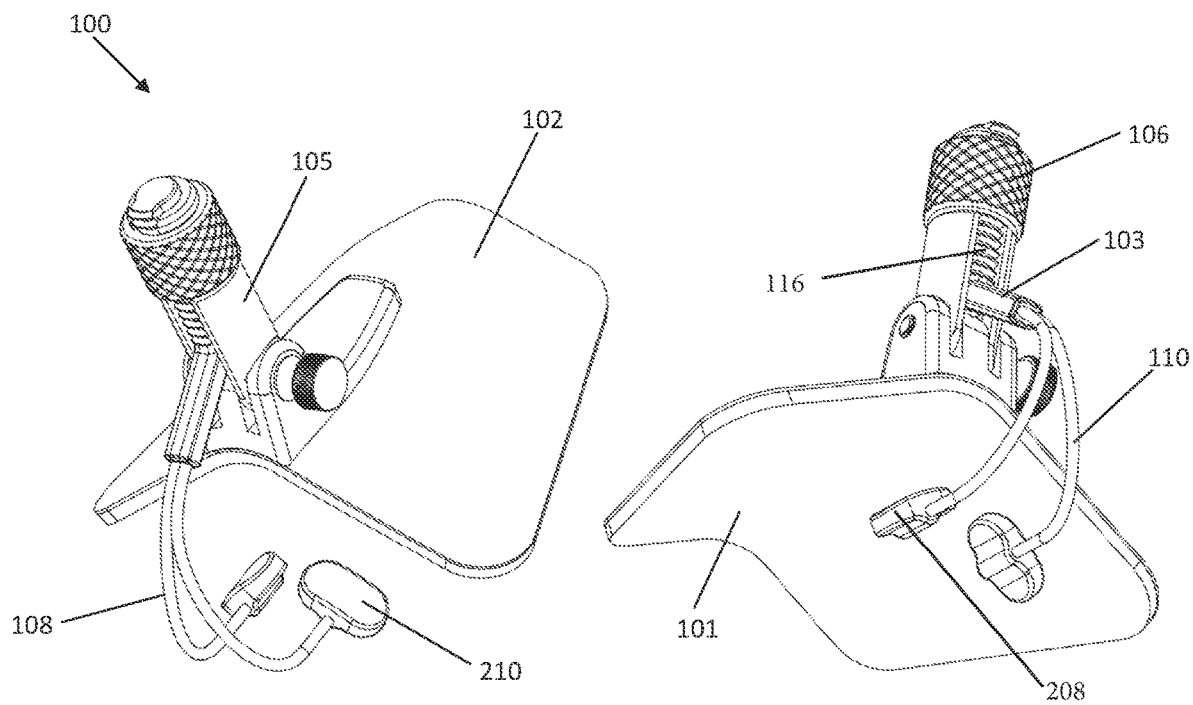
FIG. 1 is a right-side perspective view of the post-operative nasal splint, according to an example embodiment.
FIG. 2 is a bottom perspective view of the post-operative nasal splint, according to an example embodiment.
Figures 3, 4:
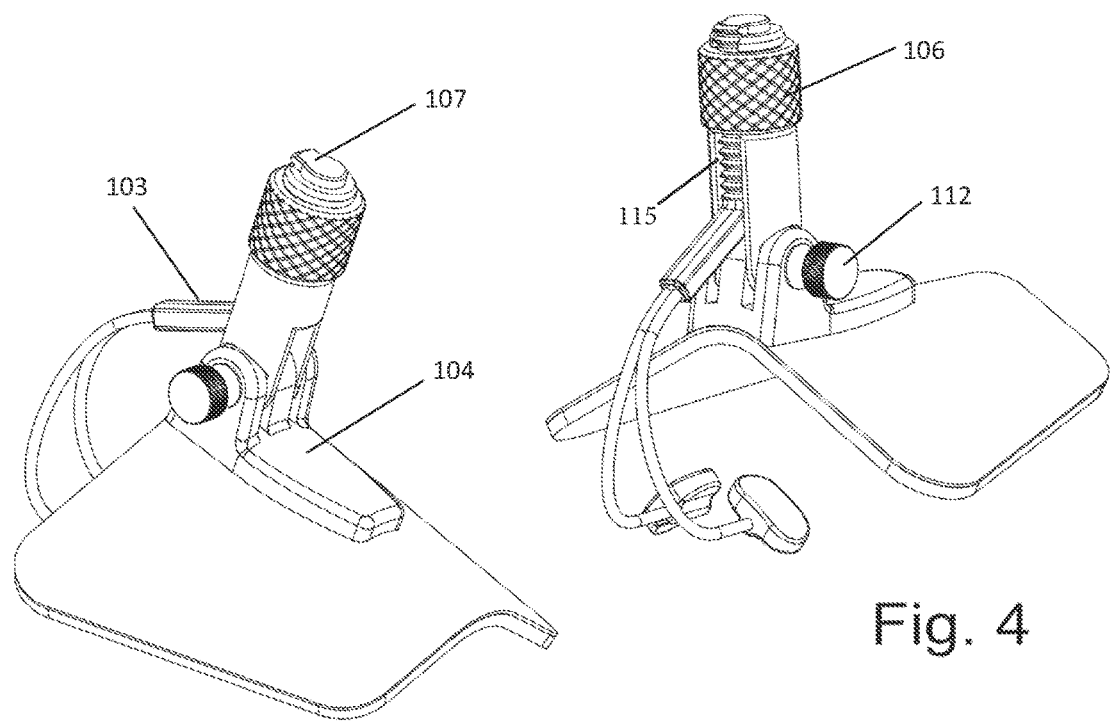
FIG. 3 is a top perspective view of the post-operative nasal splint, according to an example embodiment.
FIG. 4 is a bottom perspective view of the post-operative nasal splint, according to an example embodiment.

The following detailed description refers to the accompanying drawings. Wherever possible, the same reference numbers are used in the drawings and the following description to refer to the same or similar elements. While the claimed embodiments may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the claimed embodiments. Instead, the proper scope of the claimed embodiments is defined by the appended claims.

The disclosed embodiments improve over the prior art by providing a post-operative nasal molding splint that addresses the issue bones and cartilages of the nasal tip losing projection and changing rotation during the healing phase after a rhinoplasty. The claimed embodiments also laterally stabilize the nasal bones and allows for the reshaping of the tip and supra tip of the nose after surgery in multiple planes and directions in three dimensions. Additionally, the claimed nasal splint is also easy to handle and to utilize. Said features increase usability and proper reshaping of the nose after surgery. The disclosed embodiments also improve over the prior art by providing a post-operative nasal molding splint that reduces or eliminates unwanted movement of tissue and cartilage inwards into the face (retraction and loss of projection).

FIGS. 1-4 provide different views of the post-operative nasal splint 100, according to an example embodiment. The device 100 includes a nose splint 102 comprising a rigid curved surface shaped to fit over a dorsum of a patient's nose, wherein the nose splint comprises four straight sides with rounded edges, and wherein the nose splint includes a concave shape in one direction. The nose splint 102 includes a lower surface (or proximal surface) 101 that rests against the patient's nose and a distal surface that comprises a 104 that forms a pivot point or a hinge. The pair of malleable arms 108, 110 are configured to extend into a supratip of the patient's nose via the patient's nostrils, wherein the pair of malleable arms 108, 110 include a malleable curved shaft that is coupled to the device 100 at a proximal end, and a soft tip 208, 210, respectively, at a distal end.

The device 100 includes a tubular sleeve 105 (or tubular element), a threaded shaft (or threaded bolt element) 107 located within the tubular sleeve, and a thumb nut (or nut element) 106 located around the tubular sleeve such that the nut engages with the threaded shaft. The threaded shaft 107 is coupled to a proximal end of the pair of malleable arms 108, 110 via connector 103. The tubular sleeve 105 is configured for coupling to the nose splint 102 at the pivot point or hinge 104, wherein said pivot point is adjustable such that an angle between the tubular sleeve 105 and the nose splint 102 may be set. The tubular sleeve 105 includes a cutout 115 through which the thumb nut 106 engages with the threaded shaft 107 within the tubular sleeve. The thumb nut 106 is a tubular element having a threaded interior surface and a texturized exterior surface.

As the thumb nut 106 is rotated, it engages the threaded portion 116 of the threaded shaft 107. Depending on the direction in which the thumb nut 106 rotates, it moves the threaded shaft 107 inwards (towards the patient's face) and outwards (away from the patient's face), which, in turn, moves the pair of malleable arms 108, 110 inwards and outwards. If the thumb nut 106 is continually rotated in a first direction so that it is eventually located at a top-most location of the threaded portion 116, then the pair of malleable arms 108, 110 are located as far inwards as possible. If the thumb nut 106 is continually rotated in a second direction so that it is eventually located at a bottom-most location of the threaded portion 116, then the pair of malleable arms 108, 110 are located as far outwards as possible.

FIGS. 5-7 provide different right-side views of the post-operative nasal splint 100, showing the nasal splint in different positions, according to an example embodiment. The tubular sleeve 105 is configured for coupling to the nose splint 102 at the pivot point 104, wherein said pivot point is adjustable such that an angle between the tubular sleeve 105 and the nose splint 102 may be set. FIG. 6 shows the tubular element 105 has been rotated 301 to a downwards position, such that the angle between the tubular element 105 and the splint 102 is an obtuse angle. This allows for the rotation of the pair of malleable arms 108, 110 further into the nasal canal and provides an extra degree of freedom in adjusting the device 100 in order to assist in forming the nasal tip, supra tip and dorm post-operatively. FIG. 7 shows the tubular element 105 has been rotated 301 to an upwards position, such that the angle between the tubular element 105 and the splint 102 is an acute angle. This allows for the rotation of the pair of malleable arms 108, 110 further out of the nasal canal.

Figure 8:
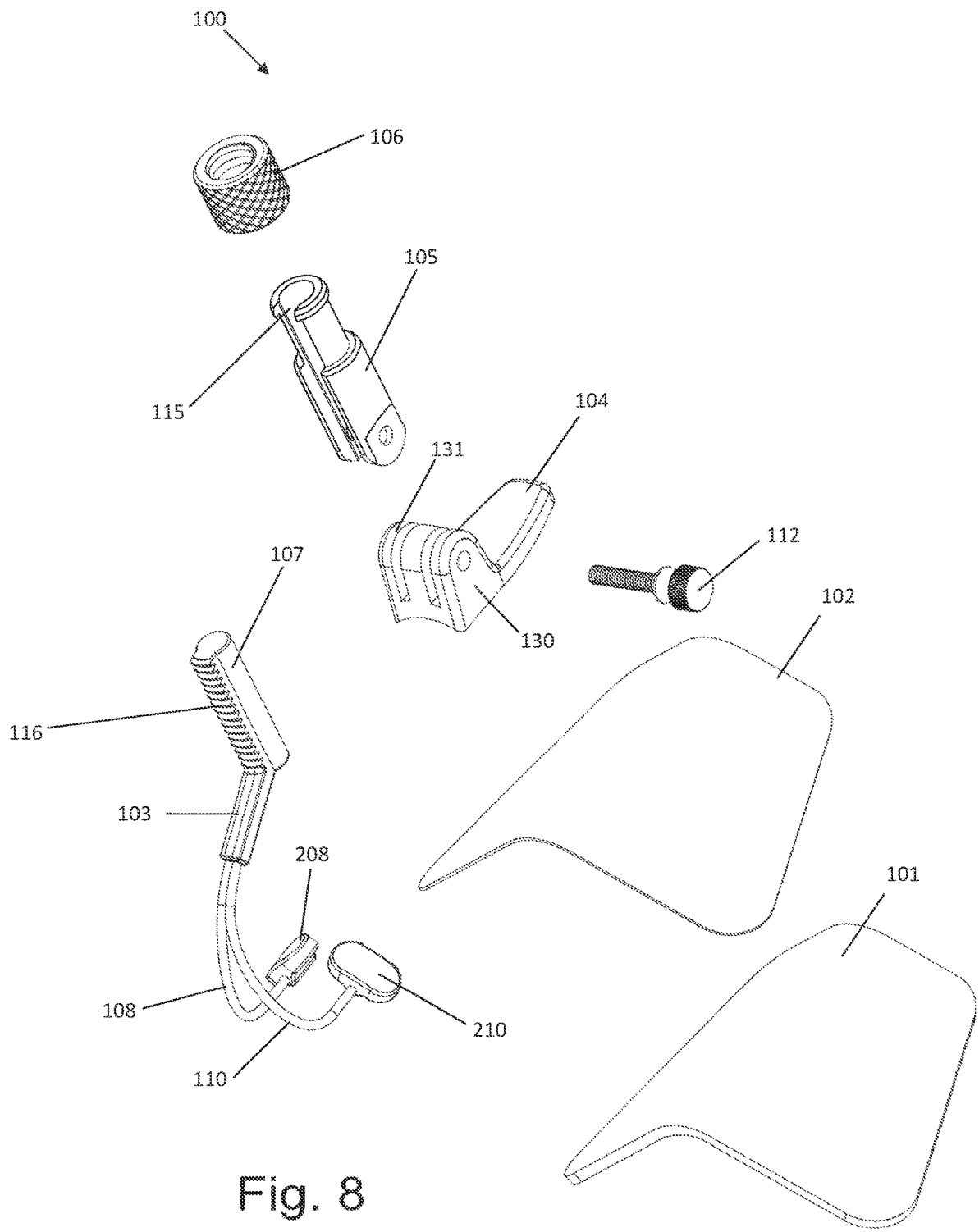
FIG. 8 is a bottom exploded view of the post-operative nasal splint, according to an example embodiment.
Figure 9:
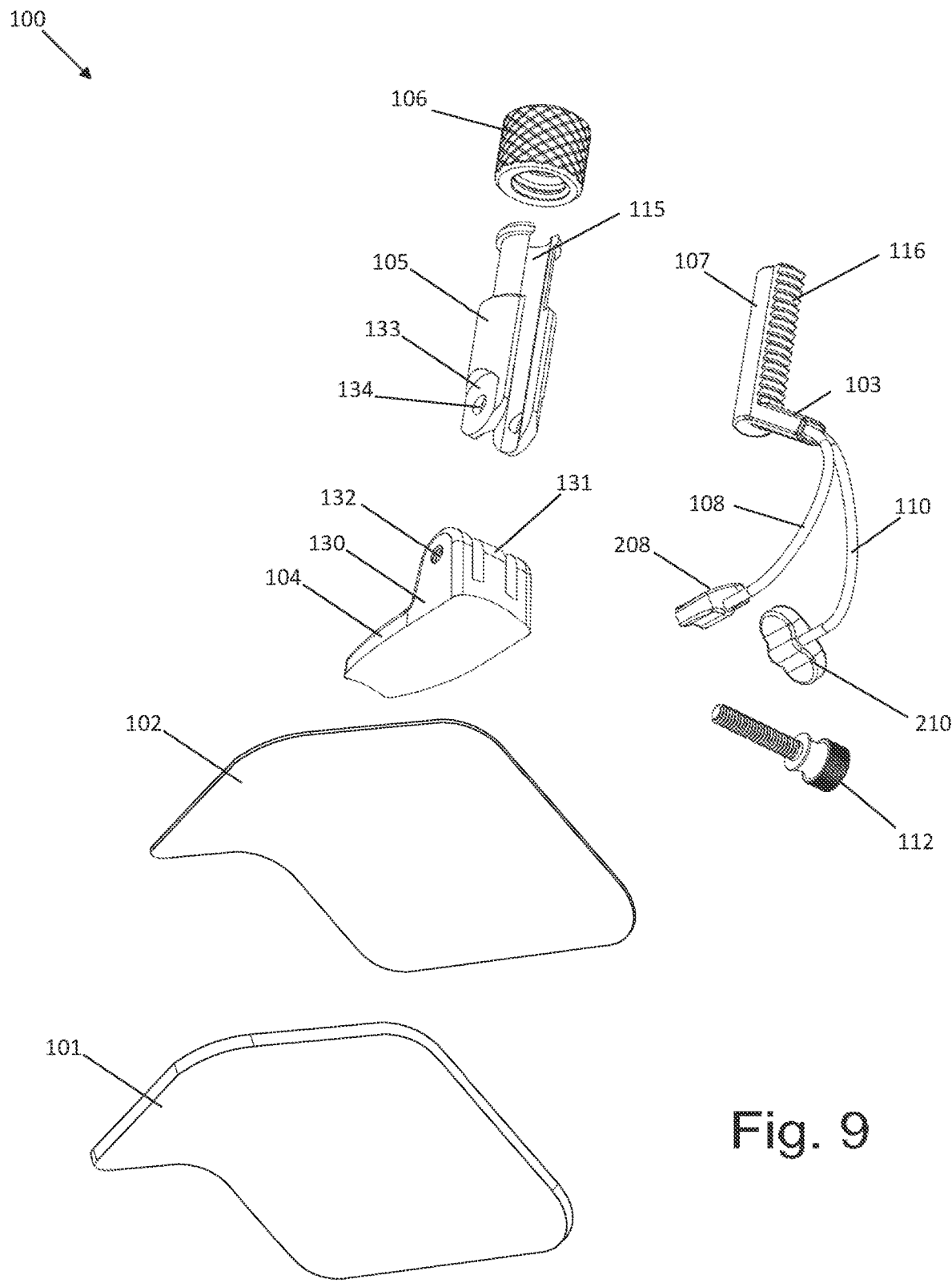
FIG. 9 is a top exploded view of the post-operative nasal splint, according to an example embodiment.

FIG. 8 is a bottom exploded view of the post-operative nasal splint 100, and FIG. 9 is a top exploded view of the post-operative nasal splint 100. FIGS. 8 and 9 show that the pivot point 104 comprises a knuckle hinge 130 comprising at least three knuckles 131 and a bore 132 extending through the knuckles. At least one of the bores within one of the knuckles includes a threaded interior surface that engages the pin described below. FIGS. 8 and 9 also show that the bottom or proximal portion of the tubular element 105 includes a pair of flanges 133, including a bore 134 extending through the flanges. When the flanges 133 of the tubular element are inserted into the spaces between the knuckles 131, the bores 132, 134 are aligned. Subsequently, the pin 112 is inserted through the bores 132, 134, thereby completing the knuckle hinge 130. The pin 112 includes a texturized outer portion that is utilized by the user to rotate the pin to thread it into and out of the bores 132, 134.

In one embodiment, at least one of the bores within one of the knuckles (such as the leftmost knuckle) includes a threaded interior surface that engages the pin 112. The pin 112 may engage with said bores within one of the knuckles that includes a threaded interior surface. The pin 112 may be rotated as far as possible, thereby tightening the pin, and tightly affixing the tubular element 105 at a specified angle with respect to the nasal splint. When said angle must be adjusted, the pin 112 may be loosened so that the tubular element 105 may be moved to its desired specified angle. Subsequently, the pin 112 may once again be rotated as far as possible, thereby tightening the pin, and tightly affixing the tubular element 105 at the new specified angle.

FIGS. 8 and 9 also show that the nose splint 102 includes a lower surface (or proximal surface) 101 that rests against the patient's nose, wherein said lower surface is similarly shaped to the nose splint and wherein the lower surface may be a malleable, soft material configured to comfortably rest against the patient's nose. Lower surface 101 may be composed of a polymeric foam such as EVA foam, LDPE foam, nitrile rubber foam, neoprene, polyimide foam, polypropylene foam, polystyrene foam, styrofoam, polyurethane foam, PVC foam, silicone foam or microcellular foam.

FIG. 10 is a bottom perspective view of the post-operative nasal splint 100 before application to a patient's nose 501. FIG. 10 shows that the tips 208, 210 have not yet been inserted into the patient's nose. FIG. 11 is a bottom perspective view of the post-operative nasal splint 100 after application to a patient's nose, according to an example embodiment. FIG. 11 shows that the tips 208, 210 have been inserted into the patient's nose via the nostrils. FIG. 11 also shows that the angle between the tubular element 105 and the splint 102 has been adjusted using the pin 112.

FIG. 12 is a bottom perspective view of the post-operative nasal splint 100 after application to the patient's nose 501 and after the splint has been formed. FIG. 12 shows that the splint 102 has been formed to match the shape and contours of the patient's nose.

In one embodiment, one or more elements of the device 100 may be composed of a plastic, such as polyolefin, polyacrylate, polystyrene, polyamide, polyvinyl alcohol, poly(alkylene acrylate), poly(ethylene vinyl alcohol), poly(alkylene vinyl acetate), polyurethane, polyacrylonitrile, polyester, fluoropolymer, polycarbonate, or combinations thereof. In one embodiment, one or more elements of the device 100, or a portion thereof, may comprise a surface that is ink-printable, i.e., the surface allows for ink printing on its surface. In another embodiment, one or more elements of the device 100, or a portion thereof, may be opaque, transparent, semi-transparent, or translucent. In another embodiment, one or more elements of the device 100 may be composed of at least one of a thermoplastic, a thermosetting polymer, polyethylene, polypropylene, polystyrene, polyvinyl chloride, polytetrafluoroethylene (PTFE), polystyrene, polyvinyl chloride, nylon, polyester, polyethylene terephthalate, high density polyethylene, polyvinylidene chloride, high impact polystyrene, or mixtures thereof. One or more elements of the device 100 may further be composed of any moldable plastic, ABS plastic, injection grade plastic, bio-plastic or biodegradable plastic. In another embodiment, one or more elements of the device 100, or any portion thereof, may be composed of rubber or a similar type of polymer.

In another embodiment, one or more elements of the device 100, or any portion thereof, may be composed of stainless steel, iron, silver, platinum, gold, zinc, copper, nickel, or any alloys or combinations of the above. The composition of the one or more elements of the device 100, or any portion thereof, may be mixed with harder metals for strength and durability.

Embodiments of the invention, for example, are described above with reference to block diagrams and/or operational illustrations of methods, systems, and processes. While certain embodiments have been described, other embodiments may exist. Further, the disclosed processes may be modified in any manner, including by reordering stages and/or inserting or deleting stages, without departing from the invention.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A medical device for facilitating post-operative nasal molding, the device comprising:
    a nose splint comprising a rigid curved surface shaped to fit over a dorsum of a patient's nose, the nose splint having a proximal surface and a distal surface;
    a tubular sleeve hingably attached to the distal surface of the nose splint;
    a pair of malleable arms movably coupled to the tubular sleeve, the pair of malleable arms configured to extend into a supratip of the patient's nose via the patient's nostrils; and
    an adjustable thumb nut coupled to the tubular sleeve and the pair of malleable arms, wherein the thumb nut is configured such that adjustment of the thumb nut moves the pair of malleable arms in a direction orthogonal to the distal surface of the nose splint.

2. The system of claim 1, wherein nose splint comprises four straight sides with rounded edges, and wherein the nose splint includes a concave shape in one direction.

3. The system of claim 2, wherein each arm of the pair of malleable arms includes a curved shaft that is coupled to the tubular sleeve at a proximal end of said arm.

4. The system of claim 3, wherein each arm of the pair of malleable arms includes a compressible tip at a distal end of said arm.

5. The system of claim 4, wherein each arm of the pair of malleable arms is coupled at the proximal end of said arm to a threaded shaft.

6. The system of claim 5, wherein the threaded shaft is movably located within the tubular sleeve.

7. The system of claim 6, wherein the adjustable thumb nut is located around the tubular sleeve such that the thumb nut engages with the threaded shaft, and wherein adjustment of the thumb nut moves the threaded shaft within the tubular sleeve.

8. The system of claim 7, wherein the tubular sleeve is hingably attached to the distal surface of the nose splint at a pivot point.

9. The system of claim 8, wherein the pivot point is adjustable such that an angle between the tubular sleeve and the nose splint may be set.

10. The system of claim 9, wherein the tubular sleeve includes a cutout through which the thumb nut engages with the threaded shaft within the tubular sleeve.

11. A medical device for facilitating post-operative nasal molding, the device comprising:
    a nose splint comprising a rigid curved surface shaped to fit over a dorsum of a patient's nose, the nose splint having a distal surface and a proximal surface configured for application to the patient's nose;
    a tubular sleeve hingably attached to a hinge protruding from the distal surface of the nose splint;
    a pair of malleable arms movably coupled to the tubular sleeve, the pair of malleable arms configured to extend into a supratip of the patient's nose via the patient's nostrils; and
    an adjustable thumb nut coupled to the tubular sleeve and the pair of malleable arms, wherein the thumb nut is configured such that adjustment of the thumb nut moves the pair of malleable arms in a direction orthogonal to the distal surface of the nose splint.

12. The system of claim 11, wherein nose splint comprises four straight sides with rounded edges, and wherein the nose splint includes a concave shape in one direction.

13. The system of claim 12, wherein each arm of the pair of malleable arms includes a curved shaft that is coupled to the tubular sleeve at a proximal end of said arm.

14. The system of claim 13, wherein each arm of the pair of malleable arms includes a compressible tip at a distal end of said arm.

15. The system of claim 14, wherein each arm of the pair of malleable arms is coupled at the proximal end of said arm to a threaded shaft.

16. The system of claim 15, wherein the threaded shaft is movably located within the tubular sleeve.

17. The system of claim 16, wherein the adjustable thumb nut is located around the tubular sleeve such that the thumb nut engages with the threaded shaft, and wherein adjustment of the thumb nut moves the threaded shaft within the tubular sleeve.

18. The system of claim 17, wherein the tubular sleeve is hingably attached to the distal surface of the nose splint at a pivot point.

19. The system of claim 18, wherein the pivot point is adjustable such that an angle between the tubular sleeve and the nose splint may be set.

20. The system of claim 19, wherein the tubular sleeve includes a cutout through which the thumb nut engages with the threaded shaft within the tubular sleeve.

* * * * *